United States Patent [19]

Catalano

[11] Patent Number: 4,731,060
[45] Date of Patent: Mar. 15, 1988

[54] HYDROSTATIC FLOAT VALVE AND INTRAVENOUS SYSTEM SUPPLIED THEREWITH

[76] Inventor: Marc L. Catalano, 2501 Bahama Dr., Miramar, Fla. 33023

[21] Appl. No.: 931,089

[22] Filed: Nov. 17, 1986

[51] Int. Cl.⁴ .............................................. A61M 5/16
[52] U.S. Cl. .................................... 604/254; 604/127; 604/49; 137/399
[58] Field of Search .......................... 604/49, 246–247, 604/251–255, 127; 137/390, 399, 433

[56] References Cited

U.S. PATENT DOCUMENTS 3,204,631  9/1965  Fields .......................... 128/DIG. 3
4,551,134 11/1985  Slavik et al. ..................... 604/247 X
4,640,306  2/1987  Fan ................................... 604/254

FOREIGN PATENT DOCUMENTS 2016897 10/1971  Fed. Rep. of Germany ...... 604/254
2509444  9/1976  Fed. Rep. of Germany ...... 604/254

Primary Examiner—Dalton L. Truluck
Attorney, Agent, or Firm—Robert M. Schwartz; Edward I. Mates

[57] ABSTRACT

This invention relates to a hydrostatic float valve for use in a fluid feed system that is capable of automatically shutting off the flow of fluid to a body cavity of a patient whenever additional or more rapid flow of said fluid would harm said patient and also relates to a fluid delivery system of the intravenous type that incorporates said hydrostatic float valve.

17 Claims, 8 Drawing Figures

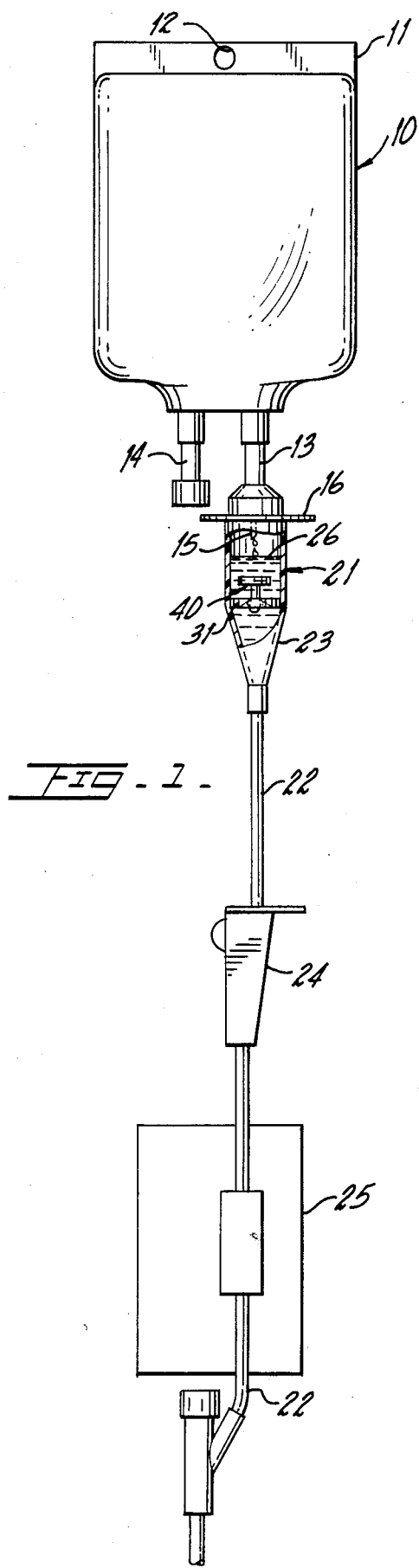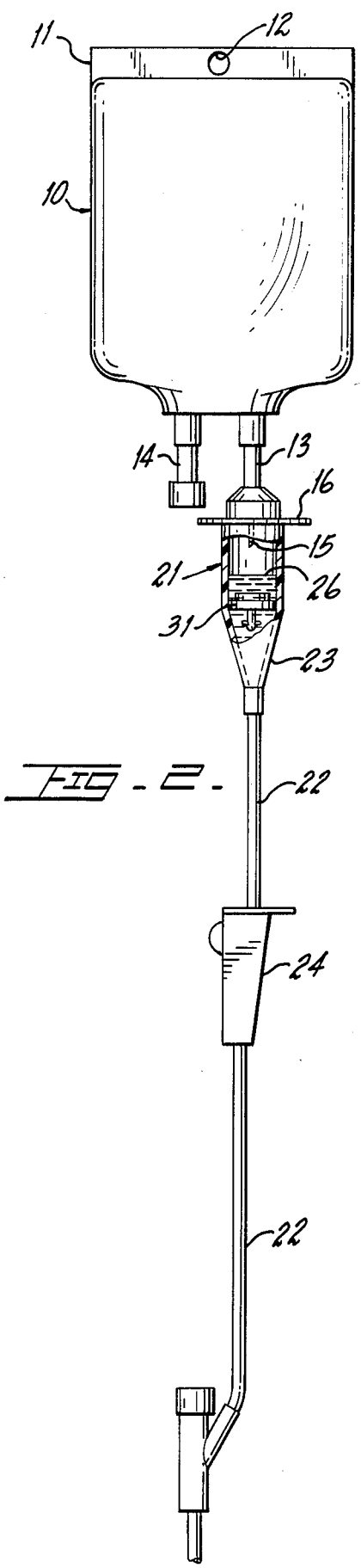

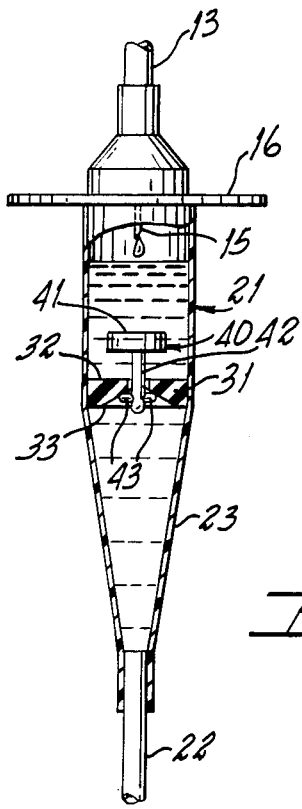
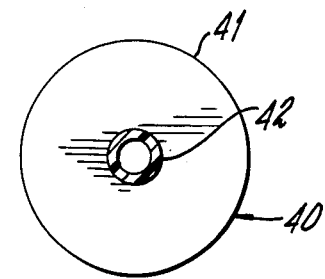
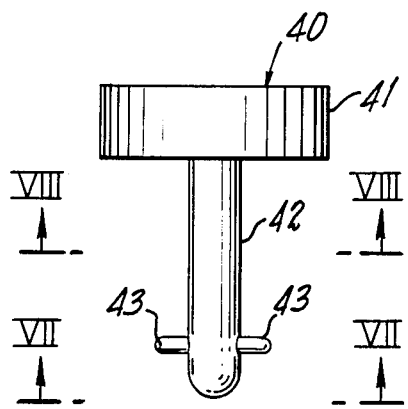
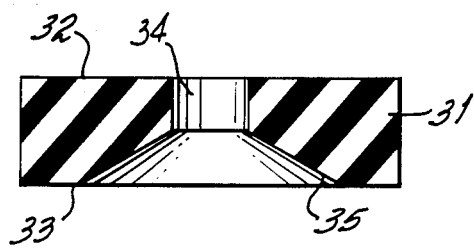
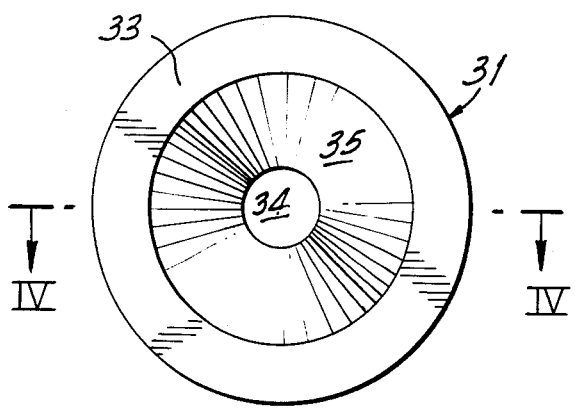
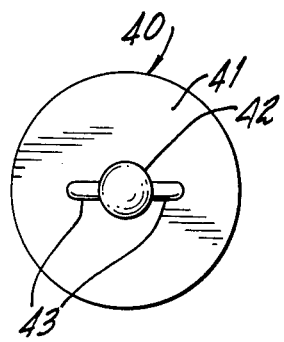

HYDROSTATIC FLOAT VALVE AND INTRAVENOUS SYSTEM SUPPLIED THEREWITH

BACKGROUND OF THE INVENTION

1. Field of the Invention

This invention relates to hydrostatic float valves, particularly those useful with fluid feed systems for supplying fluid to the body cavity of a patient and particularly those that are capable of automatically shutting off the flow of said fluid when additional flow of said fluid would be dangerous to a patient, even though a manual control valve is inadvertently left open.

2. Description of the Technical Problem

A wide range of medications, nutrients and blood are commonly administered in fluid form to patients, animal as well as human. This is done by passing fluids containing a medication or nutrient or blood at a controlled rate via a needle or catheter into the body cavity of the patient, usually through a blood vessel, and preferably a vein. The flow rate at which such fluids are infused into the patient may be critical, depending on the medication or nutrient supplied and the state of health of the patient. Furthermore, it is also usually important to control the total volume of fluid infused.

For example, excessive and/or too rapidly applied doses of certain potent drugs used to counteract certain serious problems of patients may cause serious damage and even death to certain patients. For example, Lidocane, if applied in excessive doses to stop ventricular arrhythmias, will paralyze a patient's heart and cause cardiac arrest; an excessive dose of nitroglycerine to stop angina pain by relaxing the muscles of vascular walls may cause hypovolemic shock resulting in death, as do severe doses of nipride to reduce high blood pressure. Also, excessive doses of Dopomine, used to maintain adequate systemic blood pressure in patients suffering from shock, cause vascular systems to contract, blood pressure to increase and constrict blood vessels. With more potent drugs available today than previously, it becomes more and more important to control the flow rate within the range of five to sixty cubic centimeters per hour, the exact controlled flow rate being determined by the potency of drug used and the condition of the patient.

Prior to this invention, the rate of fluid flow for intravenous administration has been controlled manually, using a manually controlled drip chamber to control the rate at which drops fall through the drip chamber. This type of control is relatively simple as it needs only gravitational forces to maintain fluid flow through the drip chamber. However, manually controlled drip chambers are not satisfactory, because it is difficult to obtain flow rate that does not deviate appreciably from the desired flow rate, particularly when the fluids are administrated over an extended time or when it is necessary to replace an empty drip chamber with another drip chamber made to dimensions within sloppy tolerance compared to the dimensions of the replaced drip chamber or to replace a first fluid with a second fluid of different viscosity. Other factors that may cause loss of control of flow rate include change in fluid pressure and vibrational influences on the drip chamber. Furthermore, unless manual control valves of prior art systems are consciously closed, no other provision is made for stopping flow automatically in case of emergency.

In order to improve the accuracy of fluid flow rates, positive displacement infusion pumps have been used. While such pumps provide more accurately controlled flow rates than manual control that are independent of variations in fluid pressure and viscosity, such pumps operate with a manual control valve set wide open in conjunction with a fluid rate controller. Such an arrangement allows infusion of medication to occur in lethal doses whenever tubing, which feeds pumped fluid medications to an inserted catheter, is removed from the controller without first shutting off the manual control valve.

Relevant Patents

U.S. Pat. No. 3,363,642 to John R. Grayson discloses a ball valve constructed and arranged to prevent flow of higher density fluids in one direction unless lower density fluid has been flowing previously for a short time in the opposite direction. The valve of this patent is useful as an auxiliary valve in a water softening device to function as an emergency shut-off to prevent unwanted flow of fresh water into a brine tank in case the main valve leaks. The auxiliary valve also prevents air from entering the softening tank after the brine tank is emptied.

U.S. Pat. No. 3,667,464 to Lawrence M. Allgood, Jr., U.S. Pat. No. 3,963,024 to Michael Goldowsky and U.S. Pat. No. 4,269,222 to Yorim Palti relate to fluid flow regulators and flow devices that control variables of flow. They comprise front valves that regulate flow rate to a predetermined setting, but are not designed to shut off a runaway system.

U.S. Pat. No. 4,449,976 to Dean L. Kamen shows a bag containing a valve that is responsive to the water level within the bag to reduce the rate of fluid flow from the bag when the water level falls to a predetermined level. This patent does not stop the water flow completely as long as water remains in the bag.

U.S. Pat. No. 4,551,134 to William H. Slavik and William B. Huber shows an intravenous set that comprises a housing that has three separate chambers, an upper valve chamber, an intermediate volumetric chamber and a lower drip chamber. An externally actuated valve member is used to interrupt the flow of fluids into the volumetric chamber. Said valve member can include a magnetically responsive element, a diaphragm or a pinch tube. The intravenous set of this patent is universally adaptable for use either as a relatively inexpensive manually controlled intravenous (i.e. IV) set or in conjunction with controller means to provide extremely accurate infusion rates. However, this patented set does not have any means for stopping infusion completely, which is important when hospital personnel is not available immediately to stop fluid infusion either in case of an emergency traumatic condition induced in the patient that requires immediate cessation of further infusion to solve the emergency or in case operating conditions of the supply system change, suddenly to make a traumatic condition of the patient imminent before help arrives.

SUMMARY OF THE INVENTION

This invention comprises a system for supplying a controlled flow of fluid to a patient and includes a special valve that is capable of either permitting gravity flow of intravenous fluid from a drip chamber to primary tubing at a restricted flow rate or stopping said flow automatically so as to avoid too much fluid being supplied to a catheter installed in a body opening of a patient even when a manual control valve is not consciously closed and an emergency happens or is imminent. The detailed construction of the special valve is an important part of this invention.

The special valve has a valve stem axially movable relative to a valve seat fixed in position within the drip chamber. The valve seat is apertured to receive the stem of the valve. The valve has a density slightly greater than that of a fluid being supplied but is sufficiently light to provide a gravity force less than the sum of the buoyant force of said fluid plus a back pressure against gravity that develops within an enclosed portion of the fluid delivery system below said special valve and above said controller and/or said manual control valve when the infused fluid is supplied to the enclosed portion at a rate faster than the outflow into the catheter so that a back pressure develops within said enclosed portion. Limiting the density of the valve body between such limits enables the valve body to be responsive to pressure reductions which occur below said valve seat whenever an intravenous infusion is inadvertently allowed to flow at an uncontrolled rate above a safe rate of flow predetermined for a given patient. The valve has an enlarged head at its upper end that rests on the valve seat opening to close the valve whenever a significant decrease in pressure is created below the valve seat due to a uncontrollable displacement of fluid that occurs when the flow rate through said enclosed delivery system portion loses control. The special valve of a preferred embodiment also has a foot at its lower portion provided with a plurality of fingers that extend radially outward from the valve stem to engage a countersunk portion of the valve seat aperture to limit upward movement of said valve by buoyancy when the combination of fluid level within the drip chamber rising sufficiently and an increase of back pressure against gravity below said valve seat cooperates to buoy said valve relative to said valve seat. One way to control the buoyancy of the valve is to make the valve stem hollow and introduce a controlled amount of fluid within the hollow valve stem.

The benefits of this invention will be understood better in the light of a description of a preferred embodiment taken in conjunction with the accompanying drawings that follows.

BRIEF DESCRIPTION OF THE DRAWINGS

FIG. 1 is an elevational view of an intravenous fluid delivery system partly in section, shown provided with a special valve in the drip chamber thereof conforming to the teachings of this invention, showing the special valve open by buoyancy and incorporating a special electronic controller and manual control valve in said delivery system;

FIG. 2 is a view similar to that of FIG. 1, showing the intravenous fluid delivery system of FIG. 1 when its intravenous tubing is detached from an infusion pump while said manual control valve is left open, thereby initiating closing of the novel valve of this invention.

FIG. 3 is an enlarged elevation, partly in section, of a drip chamber forming an important part of said intravenous fluid supply system;

FIG. 4 is an enlarged sectional view of the valve seat of FIGS. 1 to 3, taken along the line IV—IV of FIG. 5;

FIG. 5 is an enlarged top plan view of said valve seat of FIGS. 1 to 4;

FIG. 6 is an enlarged elevational view of the special valve incorporated in the intravenous fluid supply system of FIGS. 1 or 2;

FIG. 7 is a bottom view of said special valve along the line VII—VII of FIG. 6; and FIG. 8 is a cross section of said special valve along the line VIII—VIII of FIG. 6.

DETAILED DESCRIPTION OF PRESENTLY PREFERRED EMBODIMENT

In the drawings, FIG. 1 shows a main supply bag 10 of flexible material useful to store fluid to be supplied at a controlled rate as desired and whose supply is to be stopped whenever desired according to the teachings of this invention. Main supply bag 10 is provided with an apertured tab 11 at its upper portion. Tab 11 has a hook receiving aperture 12 that enables bag 10 to hang vertically when a hook (not shown) is applied through aperture 12. An outflow tube 13 and a resupply tube 14 extend downward from the bottom portion of bag 10. A thin hollow needle 15 is provided at the lower end of outflow tube 13.

A diaphragm 16 forms the roof of a drip chamber 21 of flexible material. Needle 15 pierces diaphragm 16 to permit intravenous fluid to flow by gravity from main supply bag 10 via outflow tube 13 and hollow needle 15 drop by drop into drip chamber 21. The latter communicates with primary tubing 22 through an opening in a flexible bottom portion 23 of drip chamber 21. Tubing 22 may include a manual control valve 24. Below the latter, an electronic controller 25 is optionally included along primary tubing 22 to monitor the flow rate in the primary tubing 22 and apply computer control to regulate changes in flow rate in response to deviations from a desired flow rate that are monitored. When controller 25 is used, primary tubing 22 is threaded therethrough so that controller 25 surrounds the primary tubing 22.

Controller 25 limits the mobility of a patient if installed. A catheter (not shown) at the distal end of primary tubing 22 remains applied to the patient. The latter cannot get dressed or undressed unless the primary tubing 22 is removed from the controller 25. Also, the patient cannot leave a hospital bed unless the primary tubing 22 is removed from controller 25 or the patient drags the controller 25 whenever it is desirable or necessary for the patient to walk.

Some patients observe nursing personal remove the primary tubing 22 from controller 25 and attempt to do likewise because they find the controller 25 irksome. However, the patient may be harmed if the primary tubing 22 is removed from the controller 25 improperly. Furthermore, even if the patient disengages the controller 25 properly, there is still the danger of manual valve 24 being kept open, thus enabling intravenous fluid to flow from the flexible main supply bag 10 through drip chamber 21 and the catheter at its distal end at an uncontrolled rapid rate into the patient's body. When the intravenous fluid is a potent drug, death can result to the patient if there is no stoppage of the flow rate of the potent drug into the patient's body.

The present invention avoids the perils just enumerated by installing a valve seat 31 in fixed position across the drip chamber 21. Valve seat 31 has an upper major surface 32 and a lower major surface 33, both of which major surfaces are preferably flat as shown in FIG. 4. Major surfaces 32 and 33 define a given thickness for said valve seat 31. The latter is provided with a valve seat aperture 34 extending through its thickness. Aperture 34 has a countersink 35 preferably of conical configuration, to reduce the likelihood of air bubble entrapment between the valve seat 31 and a valve 40. Countersink 35 extends upward from lower major surface 33 only part of the thickness of valve seat 31. FIGS. 4 and 5 show the valve seat structure.

FIGS. 6 to 8 show valve 40 having an enlarged upper head 41 at the upper end of a valve stem 42 and at least two radially extending fingers 43 of equal length fixed to the lower end of valve stem 42. Valve stem 42 is thinner than aperture 34 to be axially moveable through valve seat aperture 34. Valve 40 has flat upper and lower surfaces as shown in FIG. 6 and is composed of a material that has a density slightly greater than that of the intravenous fluid being dispensed. Its density is sufficiently light for valve 40 to rise from valve seat 31 in response to a pressure increase created against gravity below valve seat 31 when the closed portion below valve seat 31 is sufficiently pinched with manual control valve 24 closed to develop a back pressure against gravity below valve seat 31 that augments the buoyancy of the fluid sufficiently to lift valve 40 away from valve seat 31, yet sufficient to enable valve 40 to reengage valve seat 31 whenever fluid outflow from said enclosed portion is sufficiently more rapid than said fluid inflow to reduce the back pressure sufficiently to enable the valve to overcome the buoyancy of the fluid in the absence of a sufficiently strong upwardly directed back pressure to lift said valve. Valve stem 42 is made hollow and can be partly or completely filled with water or other fluid to control the density of valve 40.

The length of valve stem 42 between enlarged head 41 and fingers 43 is longer than the thickness of valve seat 31 to allow the upward and downward movement of valve 40 relative to valve seat 31. When fluid level 26 is relatively high in drip chamber 21, as depicted in FIG. 1, and sufficient upward pressure exists within the enclosed portion of the fluid delivery system below valve seat 31 and above controller 25 and/or manual control valve 24, valve 40 rises by buoyancy supplemented by said upward pressure to a position where enlarged valve head 41 is spaced above upper surface 32 of valve seat 31. The diameter of valve stem 42 is slightly less than that of the upper portion of valve seat aperture 34 to enable intravenous fluid from the portion of drip chamber 21 above valve seat 31 to flow by gravity through the path between valve stem 41 and valve seat aperture 34, including its countersink 35, into the flexible bottom portion 23.

The fingers 43 are shown in FIG. 7 as a diametrically opposed pair of fingers, the diametrical length of said pair being longer than the diameter of the upper portion of valve seat aperture 34 and less than the widest diameter of conical countersink 35 at valve seat lower surface 33. Therefore the fingers 43 engage countersink 35 to limit the upward motion of valve 40 caused by buoyancy when manual control valve 24 is closed and primary tubing 22 above manual control valve 24 and flexible bottom portion 23 of drip chamber 21 fills and the fluid level 26 above valve seat 31 rises to the level 26 depicted in FIG. 1. It is noted in passing that the position of fingers 43 relative to valve head 41 and the thickness of valve seat 42 are such that fingers 43 engage countersink 35 before valve head 41 reaches fluid surface 26. This feature prevents valve head 41 from engaging the fluid surface where surface tension may alter the hydrostatic characteristics of the valve.

Enlarged head 41 of valve 40 has a diameter greater than that of valve seat aperture 34. Therefore, when manual control valve 24 is open and tubing 22 below drip chamber 21 is simultaneously disconnected from controller 25 to release intravenous fluid to flow by gravity from bottom portion 23 at an uncontrolled rate, the back pressure against gravity below valve seat 31 reduces to an amount insufficient to augment the buoyant force of said fluid to continue to buoy valve 40 in spaced relation to valve seat 31. As a result, valve 40 lowers to rest on valve seat 31 and close valve opening 34. This closing of valve 40 against valve seat 31 insures that further flow of intravenous fluid into flexible bottom portion 23 stops immediately.

Once fluid flow stops by emergency action of the special valve, it is necessary to close manual control valve 24 or the open end of primary tubing 22. This closing causes the pressure within drip chamber 21 to equalize on both sides of valve seat 31. Squeezing flexible bottom portion 23 of drip chamber 21 induces an increase in back pressure within drip chamber 21 that causes valve 40 to rise and float to reopen the valve seat aperture 34. Until manual control valve 24 is closed or tubing 22 is rethreaded through controller 25, it is physically impossible to create a sufficiently strong upwardly directed back pressure below valve seat 31 to raise valve 40 to a position above valve seat 31 which allows infusion to resume. Thus the system of this invention provides an automatic stopping of fluid flow when an emergency occurs and requires a predetermined manual step to resume fluid flow when the emergency is over.

In order to use the system conforming to this invention, an operator performs a method of supplying intravenous fluid to a patient comprising: flowing intravenous fluid drop by drop by gravity into a patient via a flexible drip chamber, primary tubing having manual control valve means and a catheter, maintaining an apertured valve seat 31 of given thickness fixed within said drip chamber 21 at a level below a fluid supply level 26 within said drip chamber to divide said drip chamber into an upper portion and a flexible lower portion 23, maintaining a vertically movable float valve 40 having an enlarged upper head 41, a valve stem 42 longer than said given thickness and at least a pair of lower fingers 43 extending radially from valve stem 42, said valve stem having a specific gravity slightly greater than that of said fluid, in axially movable relation to fixed apertured valve seat 31, flowing said intravenous fluid into the upper portion of drip chamber 21, whereby enlarged valve head 41 rests on valve seat aperture 34 until said upper portion is filled with said fluid to a predetermined fluid level, closing manual control means 24, compressing the flexible lower portion of drip chamber 21 to provide a back pressure against gravity sufficient to lift enlarged valve head 41 from valve seat 31 to permit flow of said fluid by gravity from the upper portion of drip chamber 21 into the flexible lower portion, opening manual control valve 24 to flow said fluid through tubing 22 and the catheter. Fingers 43 control upward movement of enlarged valve head 41 relative to valve seat 31 so that valve head 41 floats in spaced relation to valve seat 31. The operator inspects the fluid that flows out of the catheter to determine the absence of entrapped air bubbles. When the outward flow of fluid is free of bubbles, he closes manual control valve 24 to stop outward flow of fluid, then inserts the catheter into the patient, and opens manual control valve 24 to cause said fluid to flow into the patient. Should the outward flow of said fluid from the catheter be greater than the inflow into drip chamber 21, upwardly directed back pressure in the closed portion of the fluid delivery system below valve seat 31 is reduced sufficiently to enable valve 40 to lower until enlarged valve head 41 engages apertured valve seat 31 to close valve 40 and prevent further flow of fluid into flexible lower portion 23, and into the patient.

The method aspect of this invention comprises flowing intravenous fluid drop by drop by gravity into a patient via a drip chamber, a valve, primary tubing having a closed portion, manual control means, a controller and a catheter. The valve body is selected to have a material whose specific gravity is slightly more than that of said fluid. The fluid is fed into said closed portion at a faster rate of inflow than a predetermined outflow rate to said catheter until a back pressure against gravity develops of such a magnitude in said enclosed portion that it combines with the buoyancy of said fluid to open said valve and permit further inflow of said fluid at a controlled rate into said closed portion and through said catheter to said patient. When the outflow rate races out of control, the back pressure against gravity falls automatically until the combined force of the buoyancy of said fluid and said back pressure against gravity is insufficient to prevent the valve from closing to prevent further inflow of said fluid into said closed portion. After the rate of fluid outflow is again under control, if the closed portion is of flexible material, pinching the closed portion below the valve increases the back pressure against gravity sufficiently to enable the combination of back pressure against gravity and fluid buoyancy to reopen said valve, thereby resuming a controlled rate of fluid inflow into said closed portion.

In accordance with the provisions of the patent statutes, the principle, preferred construction and mode of operation of this invention has been explained and what is presently considered its best embodiment has been illustrated and described. However, it should be understood that, within the scope of the claimed subject matter that follows, the invention may be practiced otherwise than as specifically illustrated and described.

What is claimed is:

1. A system for supplying fluid to a patient at a controlled rate of fluid flow and to stop said flow automatically when said flow rate becomes uncontrolled comprising
   a valve chamber,
   means to deliver said fluid at a controlled rate to said valve chamber,
   a valve seat fixed in position within said valve chamber to separate said valve chamber into an upper chamber portion and a lower chamber portion,
   a valve extending through said valve seat and movable relative thereto,
   primary tubing communicating with said lower chamber portion to deliver said fluid by gravity from said valve chamber to a catheter constructed and arranged for insertion into the body cavity of a patient, and
   manual valve means constructed and arranged to cooperate with said primary tubing to form a closed portion of said fluid feeding system between said valve seat and said manual valve means when said manual valve means is closed,
   characterized by the fact that said lower chamber portion is flexible to develop a back pressure against gravity when said flexible lower chamber portion is pinched while said manual valve means is closed,
   said valve has a specific gravity slightly more than that of said fluid but less than the combination of the buoyant force of said fluid and said back pressure against gravity that develops when said flexible lower portion is pinched to lift said valve from said valve seat by said combination when said back pressure is sufficiently great and to maintain said valve spaced from said valve seat as long as said back pressure is sufficiently great and to allow said valve to lower onto said valve seat when a net outflow of fluid from the closed portion of said system reduces said back pressure sufficiently until said combination of buoyancy and said reduced back pressure is so small that said valve lowers by gravity to engage said valve seat.

2. A system as in claim 1, further characterized by said valve seat having a given thickness and an aperture of given size and said valve having a valve stem narrower than and extending through said aperture and longer than said given thickness, an enlarged upper head wider than said aperture extending outwardly from the upper portion of said stem and lower fingers spaced from said upper head a distance greater than said given thickness, said lower fingers extending outwardly from the lower portion of said stem beyond the width of said aperture, the vertical distance between said enlarged head and said fingers being slightly greater than the thickness of said valve seat to limit the extent of the opening of said valve when said combination of back pressure and buoyancy is sufficient to lift said valve from said valve seat.

3. A system as in claim 2, wherein said valve seat has a flat upper surface and said enlarged valve head has a flat lower surface.

4. A valve as in claim 1, wherein said valve seat aperture has a countersunk lower portion of larger diameter than the extent of said fingers to enable said aperture to engage said fingers within the thickness of said valve seat portion.

5. A valve as in claim 4, wherein said valve seat aperture has a countersunk lower portion of conical shape.

6. A valve as in claim 1, wherein said valve comprises a hollow body at least partially filled with fluid to control the specific gravity of said valve.

7. A valve as in claim 6, wherein said hollow body is said valve stem.

8. A system for supplying a controlled flow of fluid to a patient comprising:
   a main bag useful as a fluid supply source,
   a drip chamber supported below said main bag and having an upper end portion communicating with said main bag and a flexible lower end portion, said drip chamber constructed and arranged to receive fluid by gravity from said main bag,
   primary tubing communicating with said lower end portion of said drip chamber,
   manual valve means constructed and arranged along the length of said primary tubing below said drip chamber to open and close a fluid path through said primary tubing,
   said drip chamber including an apertured valve seat fixed thereto having a given thickness and an aperture of given size extending through said thickness, said fluid path including a closed portion below said valve seat and above said manual valve means capable of developing a back pressure against gravity in an upward direction when said flexible lower end portion is pinched while said manual valve means is closed, a valve having a vertical stem narrower than and extending through said aperture and longer than said given thickness, an enlarged upper head wider than said aperture extending from the upper portion of said stem and lower fingers extending from the lower portion of said stem beyond the width of said aperture, said valve having a specific gravity slightly more than that of said fluid but less than the total force due to the combination of said back pressure and the buoyancy of said fluid so that when the fluid level rises to a predetermined level above said valve seat and said back pressure is increased sufficiently by pinching the flexible lower end portion of said drip chamber while said manual valve means is closed, said valve rises by a combined force resulting from said increased back pressure and buoyancy to a level where said fingers engage said valve seat before said enlarged valve head rises to said predetermiend fluid level to provide a restrictded passage for fluid between said enlarged head and said valve seat and through said valve seat and said lower portion of said drip chamber and through said primary tubing when said manual valve means is open to cause said back pressure to reduce sufficiently until the combination of said buoyancy and said reduced back pressure is too small to prevent said enlarged valve head from lowering to engage said valve seat and close said valve aperture to completely stop said flow of fluid into said primary tubing immediately when said combination becomes too small.

9. A system as in claim 8, further including automatic fluid control means constructed and arranged to engage said primary tubing in spaced relation to said manual valve means to control the rate of flow of said fluid through said primary tubing when said manual valve means is open and which causes loss of control of the flow rate of said fluid through said primary tubng when said control means is disengaged from said primary tubing and said manual valve means is open.

10. A system as in claim 9, wherein said automatic fluid control means engages said primary tubing below said manual valve means.

11. A system as in claim 8, wherein said valve seat aperture has a countersunk lower portion of larger diameter than that of the upper portion of said aperture to engage said fingers within the thickness of said valve seat portion.

12. A system as in claim 11, wherein said valve seat aperture has a countersunk lower portion of conical shape.

13. A system as in claim 8, wherein said valve comprises a hollow body at least partially filled with fluid to control the specific gravity of said valve.

14. A system as in claim 13, wherein said hollow body is said valve stem.

15. A method of supplying intravenous fluid to a patient comprising:

flowing intravenous fluid drop by drop by gravity into a patient via a drip chamber, primary tubing having a closed portion, manual control valve means for closing said closed portion and a catheter, maintaining an apertured valve seat of given thickness fixed within said drip chamber at a level above said closed portion and below a fluid supply level within said drip chamber to divide said drip chamber into an upper portion and a flexible lower portion, said closed portion being capable of increasing back pressure therewithin when the rate of fluid inflow into said closed portion exceeds the rate of fluid outflow therefrom and decreases when the rate of fluid outflow from said closed portion exceeds the rate of fluid inflow thereinto, maintaining a vertically movable float valve having an enlarged upper head, a valve stem longer than said given thickness and at least a pair of lower fingers extending radially from said valve stem, said float valve having a specific gravity slightly greater than that of said fluid, in axially movable relation to said fixed apertured valve seat, flowing said intravenous fluid into said upper portion of said drip chamber whereby said enlarged valve head rests on said valve seat aperture until said upper portion is filled with said fluid to a predetermined fluid level, closing said manual control valve means, compressing said flexible lower portion of said drip chamber to provide a back pressure sufficient to cooperate with the buoyancy of said fluid to lift said enlarged valve head from said apertured valve seat to permit flow of said fluid by gravity from said upper portion of said drip chamber into said flexible lower portion, opening said manual control valve to flow said fluid through said tubing and said catheter, controlling the upward movement of said enlarged valve head relative to said apertured valve seat so that said enlarged valve head is located in spaced relation above said apertured valve seat, inspecting the fluid that flows out of said catheter to determine the absence of entrapped air bubbles, and when said outward flow of fluid is free of bubbles, closing said manual control valve means to stop said outward flow of said fluid, inserting said catheter into said patient, opening said manual control valve to cause said fluid to flow into said patient, sufficiently reducing the back pressure on said enlarged valve head whenever said fluid flows from said closed portion of said primary tubing at a faster rate than it enters said closed portion of said primary tubing to permit said enlarged valve head to reengage said valve seat aperture to prevent further flow of said fluid into said flexible lower portion.

16. A method as in claim 15, further inclulding controlling the specific gravity of said float valve by selecting one having a hollow body and applying sufficient fluid into said hollow body to develop a controlled specific gravity for said float valve.

17. A method as in claim 16, wherein said selected float valve has a hollow stem, comprising applying sufficient fluid to said hollow stem to develop said controlled specific gravity.

* * * * *